US009237935B2

(12) United States Patent
McCloskey et al.

(10) Patent No.: US 9,237,935 B2
(45) Date of Patent: Jan. 19, 2016

(54) FATIGUE TESTING SYSTEM FOR PROSTHETIC DEVICES

(71) Applicant: Biomedical Device Consultants and Laboratories of Colorado, LLC, Wheat Ridge, CO (US)

(72) Inventors: Benjamin McCloskey, Evergreen, CO (US); Craig Weinberg, Denver, CO (US); Steven Weinberg, League City, TX (US)

(73) Assignee: Biomedical Device Consultants and Laboratories of Colorado, LLC, Wheat Ridge, CO (US)

( * ) Notice: Subject to any disclaimer, the term of this patent is extended or adjusted under 35 U.S.C. 154(b) by 265 days.

(21) Appl. No.: 14/137,313

(22) Filed: Dec. 20, 2013

(65) Prior Publication Data

US 2014/0109651 A1    Apr. 24, 2014

Related U.S. Application Data

(63) Continuation of application No. 12/718,316, filed on Mar. 5, 2010, now Pat. No. 8,627,708.

(60) Provisional application No. 61/158,185, filed on Mar. 6, 2009.

(51) Int. Cl.
*A61B 19/00* (2006.01)
*G01N 3/32* (2006.01)
(Continued)

(52) U.S. Cl.
CPC ............... *A61B 19/46* (2013.01); *A61F 2/2472* (2013.01); *G01M 99/007* (2013.01); *G01N 3/32* (2013.01);
(Continued)

(58) Field of Classification Search
CPC ............ G01N 3/32; G01N 2203/0089; G01N 2203/0246; G01N 2203/0204; G01N 2203/0476; A61B 19/46; G01M 99/007; A61F 2/2472
USPC .......................................................... 73/37
See application file for complete search history.

(56) References Cited

U.S. PATENT DOCUMENTS 3,911,735 A   10/1975  Di Crispino
4,381,663 A    5/1983  Swanson
(Continued)

FOREIGN PATENT DOCUMENTS

CA      2438336      2/2002
JP    08086728 A2    4/1996
(Continued)

OTHER PUBLICATIONS

Supplementary European Search Report, Application No. EP 10749376.9, Jan. 8, 2015, 8 pages.
(Continued)

*Primary Examiner* — Lisa Caputo
*Assistant Examiner* — Philip Cotey
(74) *Attorney, Agent, or Firm* — Dorsey & Whitney LLP (57) ABSTRACT

A fatigue testing system provides simultaneous cycle testing for a plurality of prosthetic devices under simulated physiological loading conditions. A plurality of sample holders containing test samples of prosthetic devices is positioned between a distribution chamber and a return fluid chamber to form an integrated test chamber. A reciprocating linear drive motor operates a rolling bellows diaphragm to cyclically pressurize fluid within the test chamber and drive the pressurized fluid through the prosthetic devices being tested. The test chamber defines a return flow conduit in fluid communication with each of the sample holders, the return fluid chamber, and the distribution chamber. Compliance chambers and throttle valves associated with each of the sample holders regulate the pressure gradient and back pressure across the prosthetic devices being tested.

13 Claims, 9 Drawing Sheets

(51) Int. Cl.
*G01M 99/00* (2011.01)
*A61F 2/24* (2006.01)

(52) U.S. Cl.
CPC ..... *G01N 2203/0089* (2013.01); *G01N 2203/0204* (2013.01); *G01N 2203/0246* (2013.01); *G01N 2203/0476* (2013.01)

(56) References Cited

U.S. PATENT DOCUMENTS

| | | |
|---|---|---|
| 4,450,710 A | 5/1984 | Nettekoven |
| 4,546,642 A | 10/1985 | Swanson |
| 4,682,491 A | 7/1987 | Pickard |
| 4,972,721 A | 11/1990 | Conti |
| 5,176,153 A | 1/1993 | Eberhardt |
| 5,272,909 A | 12/1993 | Nguyen et al. |
| 5,406,857 A | 4/1995 | Eberhardt et al. |
| 5,528,944 A | 6/1996 | Hoyt et al. |
| 5,531,094 A | 7/1996 | More et al. |
| 5,670,708 A | 9/1997 | Vilendrer |
| 5,792,603 A | 8/1998 | Dunkelman et al. |
| 6,062,075 A | 5/2000 | Ritz et al. |
| 6,810,751 B2 | 11/2004 | Moreno et al. |
| 6,881,224 B2 | 4/2005 | Kruse et al. |
| 7,254,988 B2 | 8/2007 | Keeble |
| 7,348,175 B2 | 3/2008 | Vilendrer et al. |
| 7,363,821 B2 | 4/2008 | Black et al. |
| 7,472,604 B2 * | 1/2009 | Moore, Jr. ........ G01N 3/32 73/841 |
| 7,587,949 B2 | 9/2009 | Dingmann et al. |
| 7,621,192 B2 | 11/2009 | Conti et al. |
| 8,034,608 B2 | 10/2011 | Dancu |
| 8,196,478 B2 | 6/2012 | Lorenz et al. |
| 8,318,414 B2 | 11/2012 | Dancu et al. |
| 8,584,538 B2 | 11/2013 | McCloskey et al. |
| 8,627,708 B2 | 1/2014 | McCloskey et al. |
| 2002/0116054 A1 | 8/2002 | Lundell et al. |
| 2003/0066338 A1 | 4/2003 | Michalsky et al. |
| 2003/0110830 A1 | 6/2003 | Dehdashtian et al. |
| 2003/0125804 A1 | 7/2003 | Kruse et al. |
| 2003/0143519 A1 * | 7/2003 | Perry ............... A61F 2/2472 435/4 |
| 2003/0199083 A1 | 10/2003 | Vilendrer et al. |
| 2004/0016301 A1 | 1/2004 | Moreno et al. |
| 2007/0185534 A1 | 8/2007 | Conti et al. |
| 2008/0145920 A1 * | 6/2008 | Bouten ............. A61F 2/2412 435/284.1 |
| 2009/0132043 A1 | 5/2009 | George et al. |
| 2010/0225478 A1 | 9/2010 | McCloskey et al. |
| 2011/0066237 A1 | 3/2011 | Matheny |
| 2011/0146385 A1 | 6/2011 | Weinberg et al. |
| 2011/0259439 A1 | 10/2011 | Neerincx |

FOREIGN PATENT DOCUMENTS

| | | |
|---|---|---|
| WO | WO2010/024669 A2 | 3/2010 |
| WO | WO2010/102185 A3 | 9/2010 |

OTHER PUBLICATIONS

Examination Report, Canadian Intellectual Property Office, Application No. 2,754,257, Nov. 25, 2014, 3 pages.
International Search Report and Written Opinion, Application No. PCT/US2010/061740, Sep. 9, 2011, 9 pages.

* cited by examiner

FATIGUE TESTING SYSTEM FOR PROSTHETIC DEVICES

CROSS REFERENCE TO RELATED APPLICATIONS

This application is a continuation of U.S. application Ser. No. 12/718,316 filed 5 Mar. 2010 entitled "Fatigue testing system for prosthetic devices," which claims the benefit of priority pursuant to 35 U.S.C. §119(e) of U.S. provisional application No. 61/158,185 filed 6 Mar. 2009 entitled "Apparatus and method for fatigue testing of prosthetic valves," which are hereby incorporated herein by reference in their entirety.

TECHNICAL FIELD

The technology described herein relates to systems and methods for fatigue testing of prosthetic devices, in particular, but not limited to, prosthetic vascular and heart valves, under simulated physiological loading conditions and high-cycle applications.

BACKGROUND

Prior prosthetic valve testing apparatus and methods typically use a traditional rotary motor coupled with mechanisms to produce regular sinusoidal time varying pressure field conditions. To accurately simulate physiologic conditions and/or produce a more desirable test condition, especially at accelerated testing speeds, a non-sinusoidal time dependent pressure field may be desired. This is not easily accomplished with a mechanistic approach. Furthermore, current systems employ a flexible metallic bellows or conventional piston and cylinder as drive members to provide the pressure actuation. Flexible metallic bellows are not ideal because they require high forces to operate and resonate at frequency, necessitating the use of larger driving systems and limiting the available test speeds. Piston and cylinder arrangements are not ideal because the seals employed in these systems are subjected to friction and thus have severely limited life in high cycle applications.

The information included in this Background section of the specification, including any references cited herein and any description or discussion thereof, is included for technical reference purposes only and is not to be regarded subject matter by which the scope of the invention is to be bound.

SUMMARY

A design for a fatigue testing system for cyclic, long-term testing of various types of prosthetic devices (e.g., cardiac valves, vascular valves, stents, atrail septal defect technologies, vascular linings, and others) is designed to impart a repeating loading condition for the test samples during a test run. However, the system is also designed to be variable in its abilities so it can accurately test multiple technologies. Thus, the system may be variably configured depending upon the device being tested to impart a particular loading profile to repeatedly expose the prosthetic device being tested to desired physiological loading conditions during a testing run. The purpose is to simulate typical or specific physiologic loading conditions on a vascular or heart prosthetic valve, or other prosthetic technology, at accelerated frequency over time to determine the efficacy, resiliency, and wear of the devices.

Fatigue testing is accomplished by first deploying the prosthetic device in an appropriately sized sample holder, e.g., a rigid or flexible tube, canister, housing or other appropriate structure for holding the device being tested. The sample holder is then placed between two halves of a test chamber that together form a reservoir for a working fluid. The test chamber is in turn mounted to a drive system. The sample holder and valve being tested are then subjected to physiological appropriate conditions which may include: pressure, temperature, flow rate, and cycle times.

An implementation of a drive system for the fatigue testing system may include a linear actuator or magnetic-based drive motor coupled to a flexible rolling diaphragm. The drive system is coupled to a lower opening in the test chamber and is in fluid communication with the fluid reservoir in the test chamber. The flexible rolling diaphragm (or "rolling bellow") is reciprocally moveable to pressurize and depressurize fluid and interacts with the lower section of the fluid reservoir to provide a motive force to drive the working fluid through its cycles within the test chamber, including the sample holders.

Testing and test conditions are controlled by a control computer that permits both input of test conditions and monitors feedback of the test conditions during a testing run. Computer system control may be either an open loop control that requires user intervention in the event a condition falls outside pre-set condition parameters or a closed loop control system in which the computer monitors and actively controls testing parameters to ensure that the test conditions remain within the pre-set condition parameters.

The fatigue tester is capable of simulating physiologic conditions on prosthetic devices at an accelerated rate. The fatigue tester may also be configured to create either sinusoidal or non-sinusoidal pressure and/or flow waveforms across the prosthetic devices. Pressure waveforms may also be applied that produce a pre-defined pressure gradient over time to a prosthetic device being tested.

In one exemplary implementation, a device for simultaneous cyclic testing of a plurality of prosthetic devices is composed of a test chamber, a drive motor and a fluid displacement member. The test chamber is pressurizable and has a fluid distribution chamber with a first manifold defining a plurality of ports configured to receive and fluidicly couple with a first end of each of a respective plurality of sample holders. The fluid distribution chamber also defines an aperture in a lower face in fluid communication with a pressure source. The test chamber also has a fluid return chamber with a second manifold disposed opposite and spaced apart from the first manifold of the fluid distribution chamber. The manifold of the return chamber defines a plurality of ports configured to receive and fluidicly couple with a second end of each of the respective plurality of sample holders. A fluid return conduit both structurally and fluidicly connects the fluid distribution chamber to the fluid return chamber. The test chamber also has a compliance chamber which provides a volume for holding a gas or an elastic material that compresses under a pressure placed upon fluid in the test chamber and allows fluid in the test chamber to occupy a portion of the volume. The drive motor is configured to operate cyclically, acyclically, or a combination of both. The fluid displacement member is connected with and driven by the drive motor to provide the pressure source that increases and decreases a pressure on fluid in the test chamber. In this manner, cyclic and acyclic fluid pressures may be maintained throughout the test chamber.

In another exemplary implementation, a device for accelerated cyclic testing of a valved prosthetic device includes a pressurizable test chamber. The pressurizable test chamber contains test system fluid and is further composed of a fluid distribution chamber, a fluid return chamber, a fluid return conduit, and an excess volume area. The fluid distribution chamber is positioned on a first side of the valved prosthetic device and is in fluid communication with a pressure source. The fluid return chamber is positioned on a second side of the valved prosthetic device. The fluid return conduit is both structurally and fluidily connects the fluid distribution chamber to the fluid return chamber. The excess volume area is in fluid communication with the fluid return chamber and provides a volume for storing a volume of a test system fluid when the test system fluid is under compression.

In a further exemplary implementation, a method is presented for operating an accelerated cyclic test system for evaluating a valved prosthetic device. A volume of test system fluid is stored in an excess volume area during a system driving stroke that opens the valved prosthetic device. The stored volume of test system fluid is then released during a return stroke that closes the valved prosthetic device.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention is provided in the following written description of various embodiments of the invention, illustrated in the accompanying drawings, and defined in the appended claims.

DETAILED DESCRIPTION

The system of the present invention generally includes a linear actuator or magnetic based drive coupled to a flexible rolling bellows diaphragm to provide variable pressure gradients across test samples mounted in a test chamber housing a fluid reservoir. These components operate together to act as a fluid pump and, when combined with a fluid control system, provide the absolute pressure and/or differential pressure and flow conditions necessary to cycle test prosthetic devices mounted in the test chamber. The flexible rolling diaphragm thrusts toward the lower section of the test chamber to provide a motive force to drive the working fluid through cycles within the test chamber. The flexible diaphragm is coupled to a lower opening in the test chamber and is reciprocally moveable to pressurize and depressurize fluid within the lower section of the main housing. The flexible rolling bellows diaphragm drive system has a very low inertia as compared to other drive systems, e.g., a metal bellows or a standard piston-in-cylinder drive. The flexible diaphragm is highly compliant with low resistance to axial deformation across its entire axial range of motion.

Plural sample holder tubes are coupled in parallel across the test chamber which has plural fluid distribution channels in communication with each of the sample holders. The lower distribution chamber of the test chamber has a single fluid reservoir in fluid flow communication with each of the plurality of sample holders. The distribution chamber includes a manifold with a plurality of fluid outlet ports, and each fluid outlet port communicates with an inflow opening of a test holder. The upper return chamber of the test chamber includes a similar manifold with a plurality of fluid inflow ports and compliance chambers. Each fluid inflow port communicates with an outflow opening of a respective sample holder. A central return flow channel is provided between the return chamber and the distribution chamber of the test chamber reservoir to provide a return flow of the working fluid from the outflow section of the sample holders. A throttle control and a check valve are disposed at the inflow and outflow ends of the central return flow channel, respectively, to regulate fluid flow during testing. The throttle control serves to partially regulate the pressure across the prosthetic devices being tested as well as the return flow of the working fluid in the fluid test chamber.

These components operate together to provide a differential pressure and flow conditions necessary to cycle the prosthetic device. The internal conditions, which may include, among other things, temperature, differential pressure, and system pressure, are electrically communicated to monitoring and controlling software on a test system computer. The motion of the fluid pump and therefore the system dynamics are controlled via test system control software. The pressure field resulting from the pump motion is easily controlled and can be set as a simple sine wave or as any complex user created waveform.

One exemplary implementation of a fatigue testing system 100 for any of a variety of prosthetic devices is depicted in FIGS. 1 through 5B. The fatigue testing system 100 may be understood as having two primary components, a test chamber 106 and a drive motor 105. The fatigue testing system 100 may be both partially mounted upon and housed within a base housing 157 formed and supported by a number of frame members 102. In the implementation shown, the drive motor 105 is housed within the base housing 157 while the test chamber 106 is supported on a base plate 111 forming a top surface of the base housing 157. The base housing 157 may be open on its sides or enclosed with removable panels as desired. A number of leveling feet 101 may be attached to the bottom of the base housing 157 to provide for leveling of the fatigue testing system 100 and thereby assist in creating consistent operating conditions across each of the multiple sample chambers of the fatigue testing system 100 as further described below.

Figure 1:
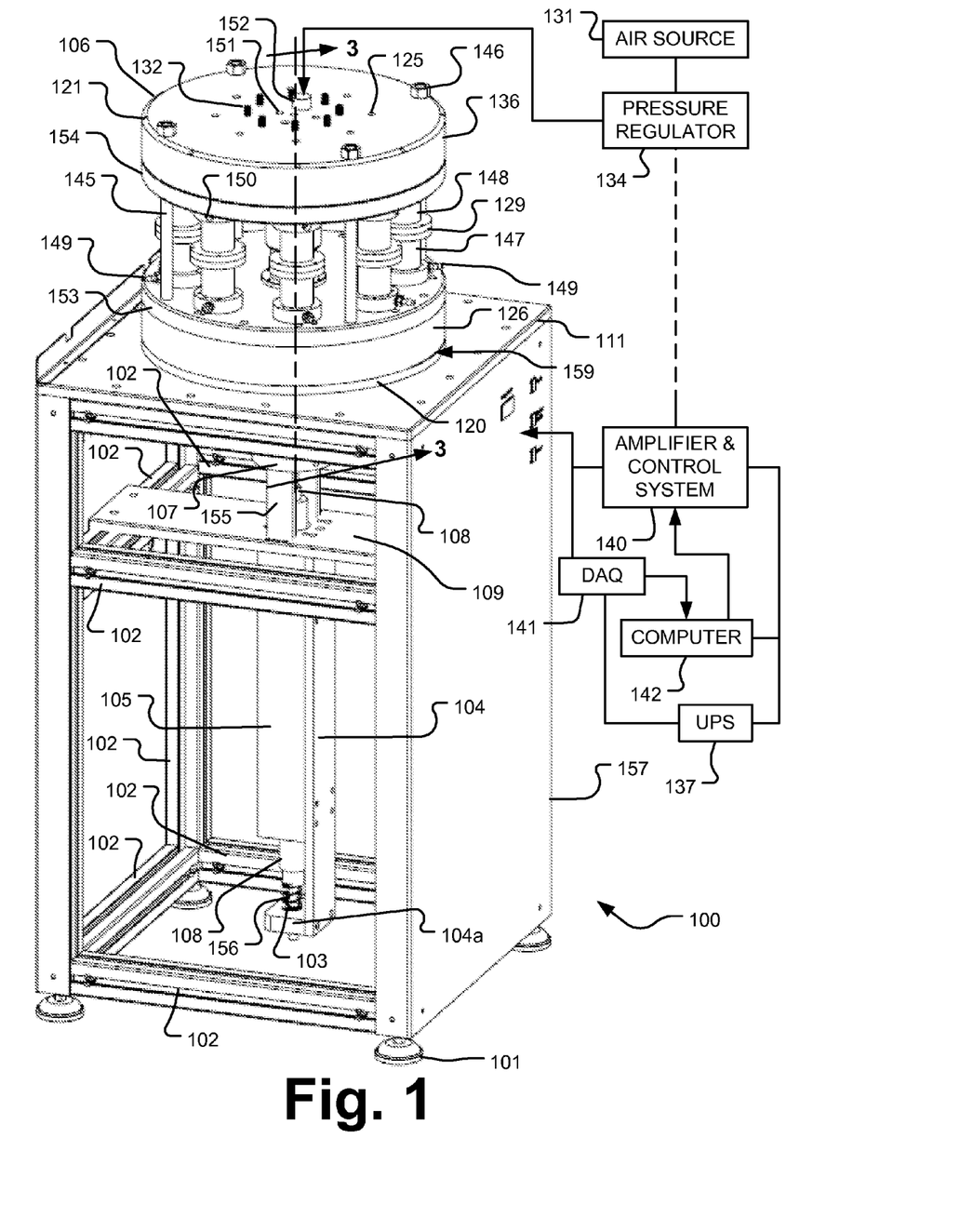
FIG. 1 is a combined isometric view and schematic diagram of an exemplary implementation of a fatigue testing system and a corresponding control system.
Figures 2A, 2B:
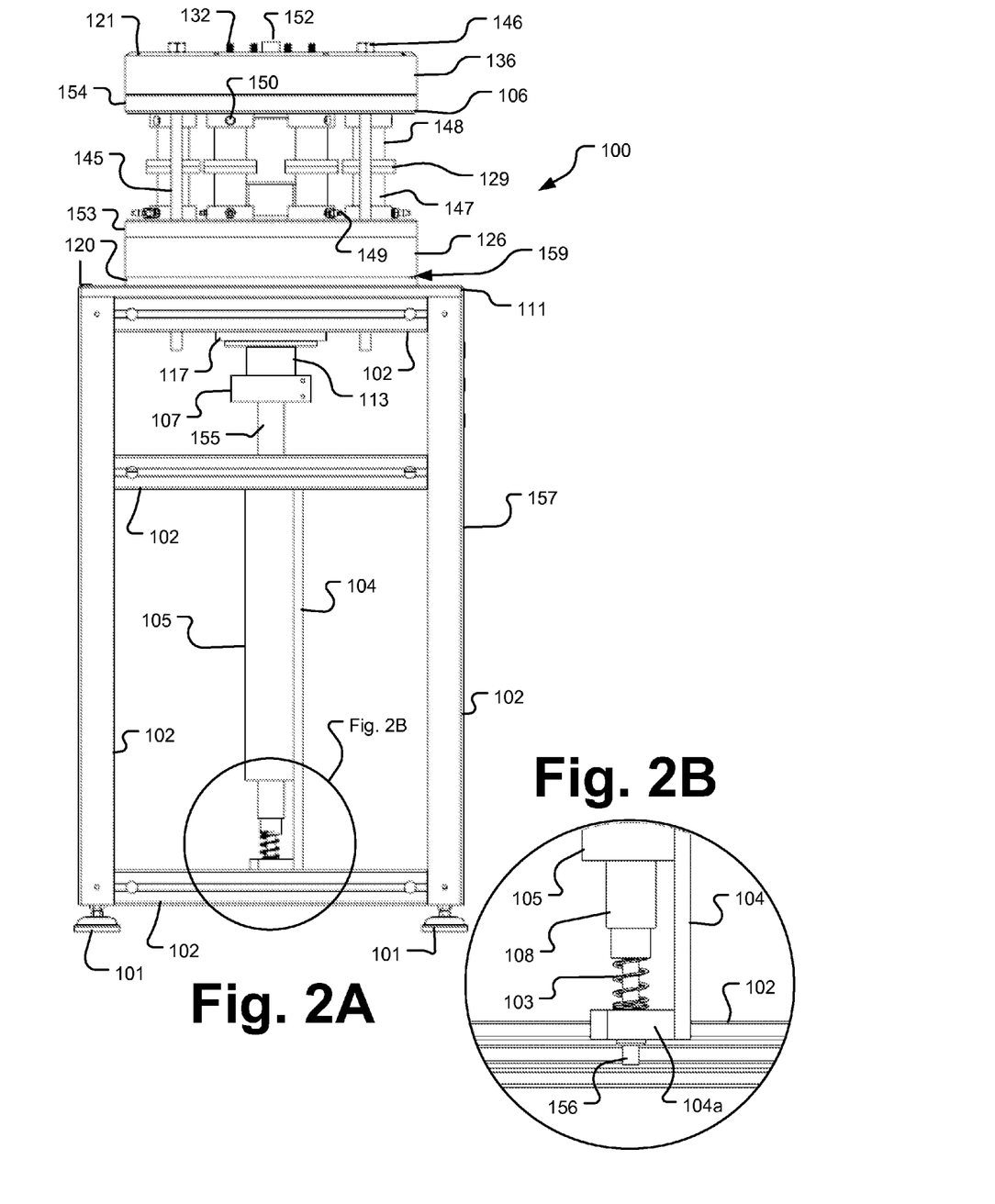
FIG. 2A is a front elevation view of the fatigue testing system of FIG. 1.
FIG. 2B is an enlarged view of the motor support in the area surrounded by the circle labeled 2B in FIG. 2A.

In the embodiment shown in FIGS. 1 and 2A with greater detail shown in FIG. 2B, the drive motor 105 may be a linear motor. The linear drive motor 105 is mounted vertically on a motor stabilizer 104 and is centered underneath the test chamber 106. The lower end of the drive motor 105 is supported by a spring 103 that interfaces with a horizontal foot 104a of the motor stabilizer 104 that extends underneath the linear drive motor 105. A lower shaft extension 156 is attached to and extends downwardly from a thrust rod 108 of the linear drive motor 105, through the spring 103, and through a bearing-lined aperture in the foot 104a of the motor stabilizer 104 where it is secured on the underside of the foot 104a as shown in FIG. 2B. The spring 103 is mounted concentrically about the lower shaft extension 156 and abuts the lower end of the thrust rod 108 of the linear motor 105 to support the weight of the thrust rod 108 of the linear drive motor 105 when the linear drive motor 105 is in an unpowered state. Further, in the event of a power failure during operation, the spring 103 prevents the thrust rod 108 from dropping quickly and causing an extremely large pressure gradient across test samples in the test chamber 106, which could damage the test samples.

The upper end of the linear drive motor 105 is fixed to a motor support plate 109 that is in turn supported by several frame members 102 of the base housing 157. An aperture in the motor support plate 109 provides for passage of the upper end of the thrust rod 108 for alignment and mechanical connection with components interfacing with the test chamber 106. It should be noted that while a linear drive motor 105 is depicted in the figures, other types of motors, for example, a regular DC motor or a voice coil, may be used to offer alternate functionality than the linear drive motor 105 of desired for a particular prosthetic device. The number of cycles completed during a test session may be monitored by a cycle counter (not shown) that monitors the motion of the thrust rod 108 of the linear motor 105, which may be affixed to the motor support plate 109.

Figure 3:
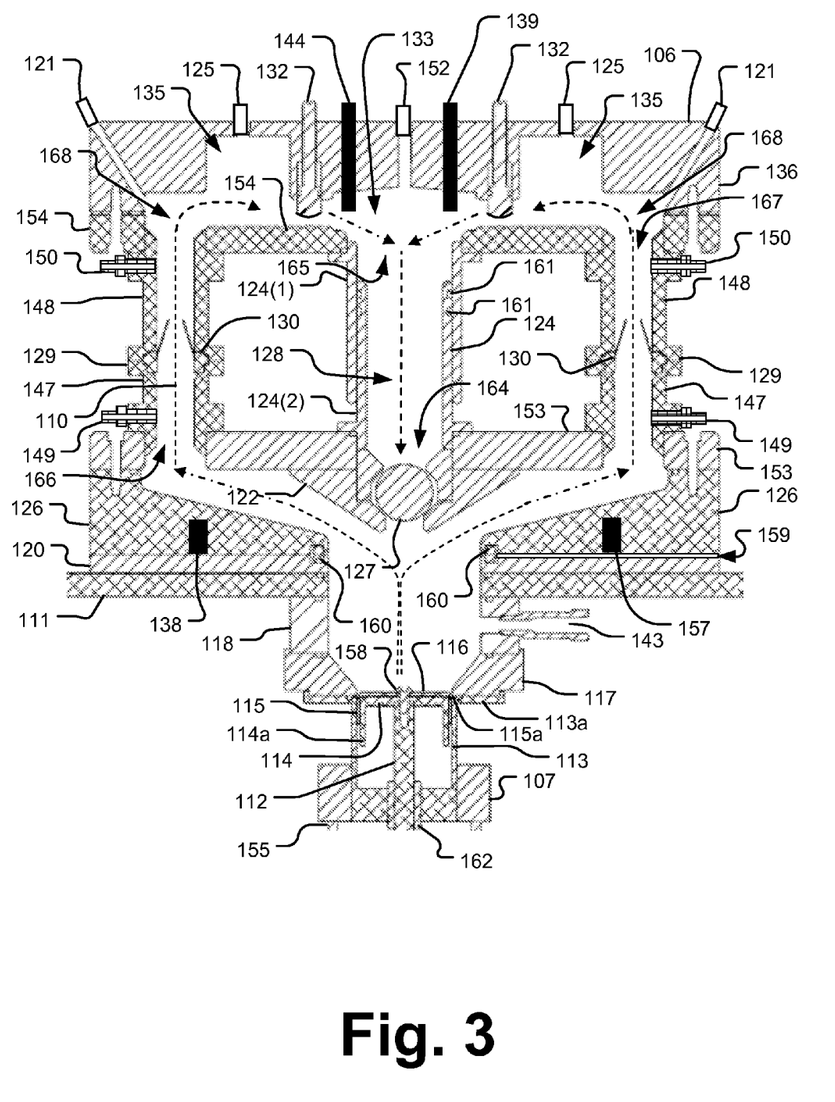
FIG. 3 is a partial cross sectional view of a test chamber of the fatigue testing system taken along line 3-3 of FIG. 1.

Several linkage components are provided between the drive motor 105 and the test chamber 106 as shown to best advantage in FIGS. 2A and 3. These components together form the drive member for creating a driving pressure on fluid in the system. An upper shaft extension 112 is fixed to and extends from an upper end of the thrust rod 108 and further extends axially within a cylinder 113. The cylinder 113 is supported about the upper shaft extension 112 within an alignment collar 107. The alignment collar 107 is further supported by a pair of alignment mounts 155 that are fixed to and extend upward from the motor support plate 109. The alignment collar 107 ensures that the cylinder 113 and the drive motor 105 maintain axial alignment.

A central aperture in the bottom of the cylinder 113 receives the upper shaft extension 112. This aperture in the bottom wall of cylinder 113 is lined with a bearing 162 to provide a low friction interface between the cylinder 113 and the upper shaft extension 112 as the upper shaft extension 112 moves within the cylinder 113 as further described below. A piston 114 in the shape of an inverted cylindrical cup may be mounted to the top of the upper shaft extension 112 for axial displacement within the cylinder 113 as the linear drive motor 105 drives the upper shaft extension 112 up and down.

The fluid drive member can be sized based on the volumetric requirements of the test chamber 106 or test samples. Depending on the volume displacement required for a particular application, the cylinder 113 and corresponding piston 114 may be swapped out for sizes of larger or smaller diameter. The cylinder 113 and corresponding piston 114 may thus be provided in a variety of diameters in order to provide different volume displacements for a given stroke, and thereby pressure differentials, within the test chamber 106 depending upon the type of sample being tested or the particular testing protocol being implemented.

The top edge of the cylinder 113 extends radially to form a flange 113a that interfaces with a bottom surface of a drive adapter 117. The drive adapter 117 may also be provided in a variety of alternative different sizes to interface with different types of cylinders 113 of various diameters. Thus, corresponding drive adapters 117 and alignment collars 107 are similarly swapped for adjustment to the size of the cylinder 113. For example, as shown in FIG. 3, the aperture in the drive adapter 117 is shaped as a frustum with a wider upper mouth toward the test chamber 106 and walls that then taper to a smaller opening at the interface with the top of the cylinder 113. In another embodiment with a larger diameter cylinder 113, the drive adapter 117 may have a larger diameter lower opening defining more sharply angled sidewalls of the frustum-shaped aperture and, in some embodiments, might even be cylindrical to accommodate a larger cylinder 113 of a common diameter.

Figure 4A:
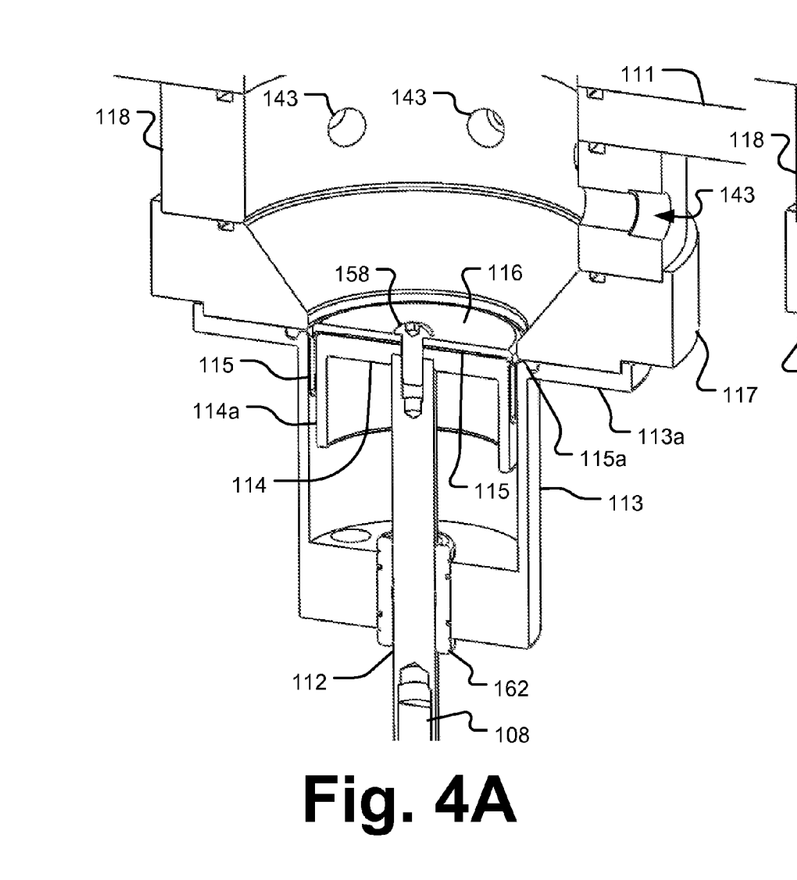
FIG. 4A is an isometric view in cross section of a portion of the fatigue testing system if FIG. 1 detailing a flexible rolling diaphragm pump connected to a linear piston drive system in a down stroke position.
Figure 4B:
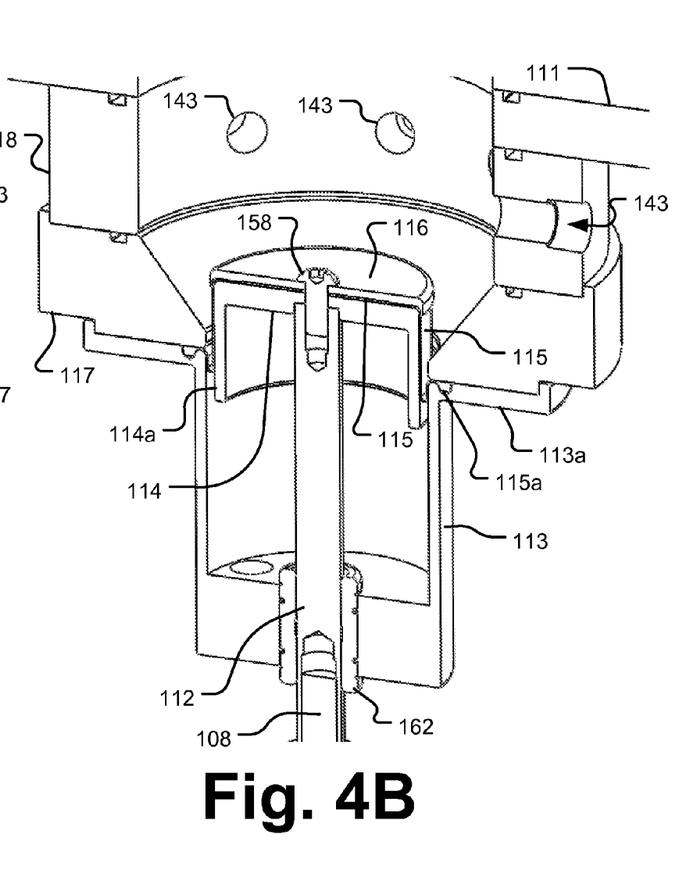
FIG. 4B is an isometric view in cross section of a portion of the fatigue testing system if FIG. 1 detailing a flexible rolling diaphragm pump connected to a linear piston drive system in an upstroke position.

In one implementation, the fluid drive member has a flexible diaphragm drive system as illustrated in FIGS. 3, 4A, and 4B. The diaphragm 115 may be a cap-like or cup-like member constructed of a non-reactive and flexible thin rubber, polymeric or synthetic based material. The flexible diaphragm 115 is highly compliant with low resistance to axial deformation across its entire axial range of motion within the cylinder 113 and the aperture in the drive adapter 117. However, alternative configurations of the diaphragm 115 may be employed so long as the configuration is capable of low friction and low resistance to deformation under the influence of the piston 114. The outer diameter of the sidewalls 114a of the piston 114 is slightly smaller than the inner diameter of the cylinder 113 to provide a uniform gap therebetween. The gap is designed to be large enough to allow the sidewall of the diaphragm 115 to fold in half against itself, i.e., evert, within this gap when the sidewalls 114a of the piston 114 are positioned within the sidewalls of the cylinder 113. It may thus be noted that in operation flexible diaphragm 115 will operate as a rolling bellows when the linear drive motor 105 is actuated.

Many advantages of a low friction flexible diaphragm 115 as opposed to a rigid metallic bellows or traditional piston and cylinder drive may be appreciated. The lateral surfaces of the diaphragm 115 evert between the sidewalls 115a of the piston 115 and the sidewalls of the cylinder 113 as the piston 114 reciprocates within the cylinder 113 and drive adapter 117. However, this eversion occurs with very low friction and low heat generation, and exerts very little resistance to piston 114 movement. As such, the drive motor can operate with a low driving force for either small or large displacements requiring low current draw and thus low energy expenditure. The flexible diaphragm 115 is highly compliant with low resistance to axial deformation across its entire axial range of motion. Alternative configurations of the diaphragm 115 may also be employed so long as the configuration is capable of very low fiction and very low resistance to deformation under the influence of the piston 114.

The cup-shaped flexible diaphragm 115 is mounted on top of the piston 114. The end wall of the diaphragm 115 is held against the top of the piston 114 by a rigid, disk-shaped cap 116, which is fastened to the upper shaft extension 112 via fastener 158 (e.g., a set screw threaded within the upper extension shaft 112). A flange surface 115a extends radially outward and circumferentially around the opening to the cavity of the cup-shaped diaphragm 115. This flange surface 115a is sandwiched between the flange surface 113a of the cylinder 113 and the bottom surface of the drive adapter 117 to maintain a pressure seal between the test chamber 106 and the drive components. In view of FIG. 3, the tapering of the frustum-shaped wall defining the aperture in the drive adapter 117 to an opening of comparable diameter to the diameter of the sidewalls forming the cylinder 113 becomes apparent, i.e., the need for corresponding surfaces between the flange of the cylinder 113 and the bottom surface of the drive adapter 117 to retain the flange surface 115a of the diaphragm 115.

A top surface of the drive adapter 117 is fastened to a plenum 118 that defines a center cylindrical aperture aligned coaxially with the aperture of the drive adapter 117 and the cavity defined by the cylinder 113. As shown in FIGS. 4A and 4B, a plurality of ports may be defined within the sidewall of the plenum 118 to provide fluid fill, drainage, or other functionality within the linkage components below the test chamber 106. For the sake of clarity, the plenum 118 shown in FIG. 3 depicts only a single sidewall port 143 that, in this embodiment, is used as a fluid inflow port. However, additional ports may be defined within the plenum 118 if desirable (see, e.g., FIGS. 4A and 4B). If not in use for a particular test configuration, the sidewall ports 143 in the plenum 118 may be plugged. The plenum 118 may be of constant diameter to interface with an aperture in the base plate 111 of the base housing 157. For this reason it can now be understood why in some embodiments the opening in the top surface of the drive adapter 117 may be of a larger diameter than the opening in the bottom surface of the drive adapter 117 as the drive adapter 117 mates with a constant diameter plenum 118 in contrast to a variable diameter cylinder 113.

As previously indicated, the test chamber 106 sits atop of the base plate 111 on the base housing 157. The foundation of the test chamber 106 may in some embodiments include a gate guide plate 120 that also defines a central aperture that is coextensive in diameter with and concentrically aligned with the aperture in the base plate 111. A distribution chamber 126 is supported by the gate guide plate 120. The gate guide plate 120, the distribution chamber 126, and the base plate 111 may all be fastened together via bolts (not shown) extending upward from the underside of the base plate 111. A pair of gate seals 160 may be positioned between the gate guide plate 120 and the distribution chamber 126. The gate seals 160 may be a set of stacked O-rings surrounding the central apertures in the gate guide plate 120 and the distribution chamber 126. The gate seals 160 may be slightly recessed within corresponding annular grooves formed in a bottom surface of the distribution chamber 126 and a top surface of the gate guide plate 120.

A shallow flat channel 159 of a width at least slightly greater than the diameter of the gate seals 160 may be formed to extend radially from the center aperture within the top surface of the gate guide plate 120. A flat rectangular knife or gate valve 119, shown to best advantage in FIGS. 5A and 5B, may be positioned within the channel in the gate guide plate 120. The gate valve 119 is shown in a radially withdrawn, open position in FIG. 5A, such that there is an open passage between the center apertures defined within the gate plate 120 and the distribution chamber 126. In this position, the gate seals 160 press against each other to create a fluid tight seal about the central apertures.

Figure 5A:
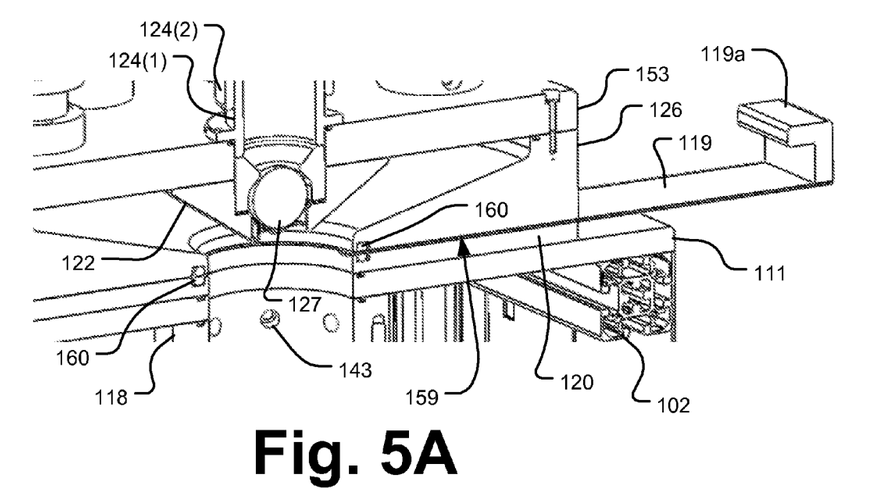
FIG. 5A is an isometric view in cross section of a portion of the test chamber of the fatigue testing system detailing an isolation valve in an open position.
Figure 5B:
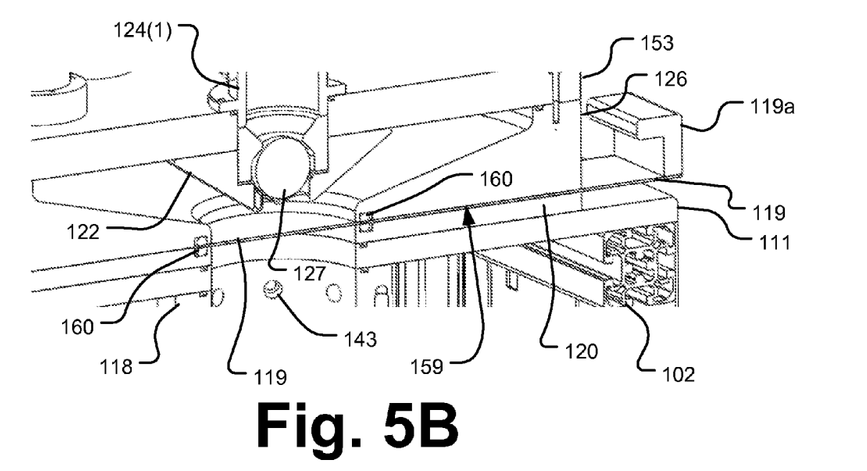
FIG. 5B is an isometric view in cross section of a portion of the test chamber of the fatigue testing system detailing the isolation valve in a closed position.

In a closed state as depicted in FIG. 5B, the gate valve 119 is pushed radially inward such that the flat plate forming the gate valve 119 extends completely across the center apertures and is sealed between the gate seals 160 to fluidically separate the gate guide plate 120 and the linkage elements below it from the rest of the test chamber 106 above it. Closure of the gate valve 119 thus allows for easy maintenance of the drive motor 105 or the piston driver 114 (e.g., replacement of the flexible bellows diaphragm 115) without having to drain the test chamber 106.

As previously noted, the distribution chamber 126 is positioned on top of the gate guide plate 120. The distribution chamber 126 defines a much wider but shallow cavity with an interior bottom wall that slants radially inward until it reaches a common diameter with the aperture of the gate plate 120. In this embodiment, one or more resistive heaters 130 may be embedded within the bulk of the distribution chamber 126 underneath the fluid cavity defined by distribution chamber 126. In one embodiment a separate heater 138 may be located immediately beneath each sample holder 129 (as further described below) to aid in the uniformity of heat distribution within the fluid in the test chamber 106.

A distribution chamber manifold 153 is mounted to a top surface of the distribution chamber 126, for example, by bolting the two surfaces together about the perimeter. The distribution chamber manifold 153 may form a conical diverter surface 122 that extends downward into the cavity of the distribution chamber 126. A center bore 164 extends through the distribution chamber manifold 153, including through the diverter 122. This center bore forms part of a return flow path 128 as further described below. The distribution chamber manifold 153 may further define a plurality of bores 166 spaced about the perimeter of the distribution chamber manifold 153. In the embodiment shown in FIGS. 1 through 3, eight perimeter bores 166 are defined at a uniform radial distance from the center and are equiangularly spaced apart. However, in alternative embodiments, there may be greater or fewer perimeter bores 166 and different or non-uniform spacing may be implemented if desired. A sample inlet tube 147 forming the bottom half of a sample holder 129 is connected within and seals against each of the perimeter bores 166 of the distribution chamber manifold 153.

Similarly, a lower conduit wall 124(2) of a telescoping center conduit 124 mounts within and seals against the center bore 164 in the distribution chamber manifold 153. A one-way valve 127 or similar check valve is positioned within the center bore 164 of the distribution chamber manifold 153 below the lower conduit wall 124(2) of the center conduit 124. The second half of the center conduit 124 is formed as a cylindrical upper conduit wall 124(1) with an inner diameter substantially the same as an outer diameter of the lower conduit wall 124(2) such that the center conduit 124 can be expanded or contracted in length. One or more center seals 161, for example, in the form of O-rings mounted within annular recesses in the outer surface of the lower conduit wall 121(2) provide a fluid tight seal interface with the interior surface of the upper conduit wall 124(1).

Each of the sample holders 129 is also composed of a sample outlet tube 148 that sits atop a respective sample inlet tube 147. The actual test sample 130 (e.g., a prosthetic device) may be sandwiched between the sample inlet tube 147 and sample outlet tube 148 to hold it in place within the test chamber 106. In other embodiments (not shown) each of the sample holders 129 may be an integral unit with a test sample 130 mounted within by any of a variety of means that may be specific to the nature of the particular test sample 130.

A return chamber manifold 154 is positioned atop each of the sample outlet tubes 148 and the upper conduit wall 124(1) of the center conduit 124. The return chamber manifold 154 defines corresponding perimeter bores 167 for mating with each of the sample outlet tubes 148 and a center aperture 165 for mating with the upper conduit wall 124(1) of the center conduit 124. Each of the interfaces between the sample outlet tubes 148 and the center conduit 124 with the return chamber manifold 154 is configured to provide a fluid tight seal between the components.

A return chamber 136 is mounted on top of the return chamber manifold 154 in a similar manner as the distribution chamber 126 is mounted to the distribution chamber manifold 153. The return chamber 136 defines one or more compliance chambers 135 which, in the embodiment of FIGS. 1-3, are composed of cavities associated respectively with each of the sample holders 129. As used herein, "compliance" refers to the ability of the cavities forming the compliance chambers 135 to absorb some of the pressure placed upon the fluid in the test chamber 106 and further to control recoil toward the original volume dimensions upon removal of the compressive force. The compliance chambers 135 assist in minimizing the effects of large and quickly changing pressure gradients across test samples 130 placed within the test chamber 106. In some implementations, the compliance chambers 135 may merely contain air or another gas. The air or other gas may be indirect contact with the working fluid in the test chamber 106 or a membrane may be provided within the compliance chambers 135 to separate the air or gas from the working fluid. In other embodiments, the compliance chambers 135 my house a porous material or an elastomeric material. In each case, the purpose of the compliance chambers is to act as a resilient spring force to dampen the effects of large, quickly changing pressure gradients within the test chamber 106.

The return chamber 136 further defines separate return conduits 168 that are in fluid communication with respective pairs of the sample holders 129 and compliance chambers 135. A respective throttle valve 132 is housed within the return chamber 136 and placed between each respective return conduit 168 and a central return basin 133 that empties into the center return conduit 124. Each of the throttle valves 132 may be operably raised or lowered to restrict or enlarge the fluid flow passage between the return conduits 168 and the central return basin 133 and assist in the regulation of the pressure across the test samples 130 in the sample holders 129.

The return chamber 136 may also define a number of bores variously in communication with the return conduits 168, the compliance chambers 135, the central return basin 133. For example, system input bores 121 may be provided for relatively direct access to each of the sample holders 129 via the return conduits 168. The system input bores 121 may be used for a variety of purposes, for example, for the placement of sensing or diagnostic equipment or for access to the test samples 130 in the sample holders 129. In a particular example, when testing a valve design with removable valve leaflets, the system input 121 could be used to access the sample holder 129 and remove and replace the valve leaflets while leaving the permanent valve mounting structure in place within the sample holder 129. This obviates the need to disassemble the test chamber 106 for replacement of components of the test samples 130.

An access port 125 may also be associated with each of the compliance chambers 135. The access port 125 may be used for the attachment and introduction of sensing equipment or for providing additional air or gas pressurization to the compliance chambers 135. Additional sensors may further be placed in access ports positioned for communication with the central return basin 133. For example, as shown in FIG. 3, a temperature transducer 139 and a water level sensor 144 may be placed in communication with the central return basin 133. It should be understood that any number of other sensor devices could also be placed in contact with or introduced within the test chamber 106 by any of the various apertures, bores, or ports provided within the return chamber 136.

The various sensors of the fatigue testing system 100 may be operably connected to a data acquisition (DAQ) device 141. An amplifier and control system 140 may also be connected with the drive motor 105 to provide output control of the same. In some embodiments, the DAQ device 141 and amplifier/control system 140 may be mounted within the base frame 157. An air source 131 connected in line with a pressure regulator 134 may also be under control of the control system 140. These components are, in turn, either directly or indirectly operably connected to a microprocessor-based computer 142. All systems may also be connected to an uninterrupted power supply (UPS) 143.

Software provided on the computer 142 can direct the system controller 140 to provide full closed-loop control based on feedback measurements received from the DAQ device 141 coupled with the sensors. In one example of this functionality, software may be configured to control the driving amplitude and velocity of the drive motor 105 based upon differential pressure transducer feedback. The system 100 may therefore compensate for any changes during the high cycle testing cycle providing the test samples 130 with the most optimal testing conditions. An automated test interface may be provided as part of the fatigue testing system 100 to run the test chamber 106 without direct management, ensuring proper testing conditions and safety mechanisms. The test interface may be configured to provide closed-loop control based off any system measurement feedback.

An implementation of operation of the exemplary fatigue testing system 100 of FIGS. 1-5B may be understood as follows. Initially, test samples 130 need to be placed within the test chamber 106. In order to introduce test samples 130, the sample holders 129 must be accessed. The adjustment nuts 146 on the top of the return chamber 136 may be rotated to raise the adjustment posts 145 from their tightened positions within the distribution chamber manifold 153 and distribution chamber 126. Once the return chamber 136 and return chamber manifold 154 are raised, the sample holders 129 may be removed and replaced with alternate sample holders or, as shown in this embodiment, samples positioned between sample inlet to 147 and sample outlet to 148, may be removed and replaced with new samples 130. The adjustment nuts 146 may then be tightened to lower the return chamber 136 and return chamber manifold 154 back into contact with the sample holders 129 to create fluid-tight flow path through each of the sample holders 129 between the distribution chamber 126 and the return chamber 136. Note that when the return chamber 136 and return chamber manifold 154 are raised, the center conduit 124 telescopes upward with the upper conduit wall 124(2) sliding along the exterior of the lower conduit wall 124(1), thus maintaining a fluid-tight connection within a center conduit 124.

In many applications, it may be desirable to monitor the pressure gradient across the sample holder 129. For such purposes, a conduit with a sensing device, for example, a pressure transducer, may be placed in a conduit that is attached at one end to a monitor outlet port 149 in the sample inlet tubes 147 and a monitor inlet port 150 on the sample outlet tubes 148. In an alternative implementation, individual sensors (e.g., pressure transducers) may be attached directly to each of the monitor outlet ports 149 and monitor inlet ports 150 to measure absolute pressure at each of these locations. The absolute pressure data may be collected by the data acquisition component 141 and transferred to the computing device 142 for calculation of the pressure differential by taking the difference between the absolute pressure values on either end of the sample holders 129.

Presuming that the correct size of cylinder 113 and corresponding drive adaptor 117 are already attached, the fatigue testing system 100 may be charged with the desired type and amount of working fluid through any one of the inflow ports 143 in the plenum 118. The working fluid may be water, saline, a saline/glycerin solution, a glycerin/water solution, a blood analog or substitute, or other type of fluid. In some embodiments, the working fluid may be selected to simulate one or more attributes of human blood, such as density, viscosity or temperature. For example, in certain instances, physiological saline which does not simulate the viscosity of blood, but simulates density, may be used. In other cases saline/glycerin solution may be employed to simulate blood viscosity.

Depending upon the particular test samples 130 and desired testing conditions and dynamics, the fatigue system 100 may be filled with fluid up to an appropriate or desired level in the compliance chambers 135. Once fluid has been filled to a desired level, in some scenarios, the fatigue testing system 100 may be additionally pressurized with air or another gas via an air source 131, e.g., an air compressor or sealed pressurized volume, connected to the air inlet 152 in the return chamber 136 or via the compliance access ports 125 in the compliance chambers 135. In some embodiments, a pressure regulator 134 may be interposed between the air source 131 and the air inlet 152 to regulate the pressure within the test chamber 106. Alternatively, the system 100 can be pressurized by first sealing the system 100 and then changing the position of the fluid driving piston 114 such that the available volume is decreased.

The working fluid temperature is controlled via the fluid heaters 138 and the temperature transducer 139. Upper and lower temperature bounds may be set in the test software. At startup the system 100 will begin to heat until the upper bound is reached. As the input temperature falls below the lower bound, the heaters 138 are again activated, thus maintaining a mean temperature within acceptable bounds. This mean temperature is typically set to 37° C. to simulate physiologic conditions.

Once the system is filled with fluid, heated, and properly pressurized, testing operations under control of the computer 142 may be initiated. The computer 142 may control the operations of the linear drive motor 105 to move the piston 114 and thus the diaphragm 115 up and down within the cylinder 113 and drive it after 117 to cyclically increase and decrease the pressure within the test chamber 106. Under computer control and depending upon the size of the cylinder 113, the linear drive motor 105 may cause the thrust rod 108 and the attached upper shaft extension 112 to move up and down thereby moving the cylinder 113 and diaphragm 115 up and down to create a displacement of any size, small or large, to change the pressure within the test chamber 106. The rolling or eversion of the diaphragm 115 exerts very little resistance to piston 14 movement. Thus, power requirements on the linear drive motor 105 are small and current draw is minimized.

Fluid flow 110 through the test chamber 106 is indicated by the dashed lines initiating at the drive adaptor 117 traveling through the plenum 118 and then through the sample holders 129 to exit through the return conduit 168, the central return chamber 133, and the center conduit 124. Fluid flow can be prevented from moving upward in the center conduit 124 by the one-way valve 127 housed within the distribution chamber manifold 153. The conical diverter 122 helps direct fluid flow from the piston 114 regularly and uniformly to each of the sample holders 129 about the perimeter of the test chamber 106.

The compliance chambers 135 provide excess volume area for fluid to move into when the piston 114 performs a compression stroke. As the pressure of the gas in the compliance chamber 135 increases, the volume occupied by the gas decreases to provide additional volume for displacement of the liquid working fluid within the test chamber 106. The throttle valves 132 restrict the rate of return flow of fluid within the test chamber 106 into the central return basin 133. The combination of the compliance chambers 135 and the throttle valves 132 help control undesirable pressure loading or pressure spikes within the sample holder 129 and consequent adverse effects on the test samples 130 when the piston 114 moves in a decompression stroke. The compliance chambers 135 and the throttle valves 132 also generally help tune the test conditions across the sample holder 129. In addition to selecting the piston size, the displacement range, frequency, and waveform settings, the system equilibrium pressure, and other settings, the compliance chambers 135 and the throttle valves 132 may be adjusted as an additional aid in fine-tuning appropriate differential pressure across the test samples 130 in the sample holder 129.

As the piston 114 moves downward in decompression stroke, pressure on the one-way valve 127 is released and fluid flow through the center conduit 124 is initiated at a controlled rate depending upon the position of the throttle valves 132. In this way, on the downward stroke, the pressure in the test chamber 106 returns to an initial level and excess volume returns to the compliance chambers 135. It should be noted that the compliance chambers 135 may be configured in a variety of different ways. In addition to merely containing a volume of air or other gas to act as an air spring, a membrane could be provided between the liquid and the air or other gas or alternatively the space could be filled with a porous foam or other elastomeric material, thereby reducing or otherwise adjusting the spring factor provided by the compliance chamber 135.

The dynamics of the system 100 can be controlled through the stroke pattern, frequency, and volume of the piston 114, the flow setting of the throttle valves 132, and the spring force of the compliance chambers 135. Additionally, the working fluid in the test chamber 106 may be preset to a base or ambient pressure using a separate pressure source. For example, an air/gas source 131 (e.g., and air compressor or gas tank) may be connected to and pressurize a fluid reservoir (not shown) in fluid contact with the working fluid in the test chamber 106. A pressure regulator 134 may be positioned between the air source 131 and the introduction into the test chamber 106 for controlling the desired system pressure. Alternatively, a pressurized gas may be introduced directly into the compliance chambers 135 through access ports 125, into the central return basin 133 through inlet 152, or through any other port (e.g., one of the sidewall ports 143 in the plenum 118) for charging the test chamber to an appropriate base pressure for proper function of the system 100 for the particular test configuration.

Figure 6:
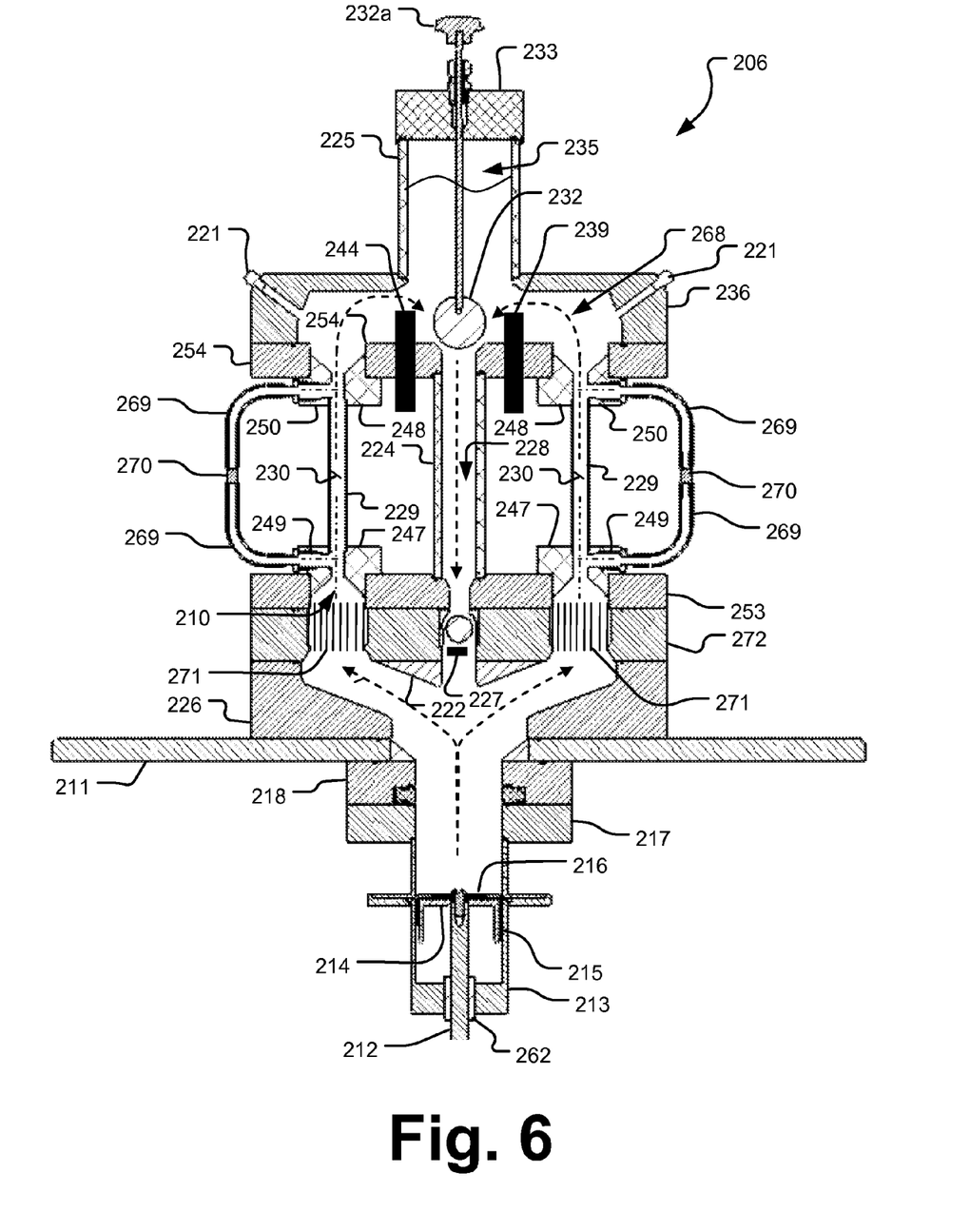
FIG. 6 is a schematic diagram in cross section of an alternative implementation of a test chamber for use in a fatigue testing system.

An alternate embodiment of a test chamber 206 for a fatigue testing system 200 is shown in FIG. 6. The test chamber 206 consists generally of a lower chamber composed of a distribution chamber 226, a flow conditioning chamber 272, and a manifold 253, and an upper chamber composed of a return chamber 236, a manifold 254 and a central compliance chamber 235. A fluid flow pathway 210 extends from the lower chamber to the upper chamber which passes through a plurality of sample holders 229 holding the device samples 230 being tested and a return fluid flow pathway 228 extends from the upper chamber to the lower chamber to return fluid from the upper chamber to the lower chamber in preparation for a following cycle. A check valve 227 is inline with the return fluid flow pathway 228 between the upper and lower chambers to regulate back flow through the test chamber 206. A controllable central throttle valve 232 is also in-line with the upper and lower chambers to regulate the differential pressure across the test samples 230 during operation.

The fluid drive member, i.e., the piston 214, is provided within the cylinder 213 to pressurize and drive the working fluid upward through the drive adapter 217 and the plenum 218. The piston 214 is mounted on the shaft extension 212 extending through the bearing 262 from the thrust rod of the linear motor (not shown). The flexible diaphragm is mounted on the piston 214 as in the prior embodiment and held in place by a cap 216. The diaphragm 15 is preferably a cap-like member constructed of a non-reactive and flexible thin rubber, polymeric or synthetic based material. The lateral surfaces of diaphragm 215 roll or evert as the piston 214 reciprocates within the cylinder 213 and drive adapter 217 between which the circumferential flange of the diaphragm is sealed. These components are affixed to the support plenum 218 and maintain the pressure seal along the circumference of the diaphragm 215. The plenum 218 serves as a mounting point for the drive system. The plenum 218 may also include fluid ports for pressure monitoring and system draining.

During the primary or pressurization portion of a test cycle, the piston 214 moves in a positive direction toward the test chamber 206 and creates an initial pressurization and the working fluid flows up through the base plate 211 into the distribution chamber 226. The working fluid impinges upon a generally conical flow baffle 222 and is directed radially outward to flow straighteners 271. The fluid is blocked from entering the central return conduit 224 by a one-way exit valve 227. The working fluid then passes from the distribution chamber 226 and into a flow conditioning chamber 272, wherein it passes through a flow straighteners 271, aligning the flow along the axis of the sample holders 229. Sample adapters 247, 248 attach the sample holders 229 to the distribution manifold 253 and the return manifold 255, allowing the sample holders 229 to be connected to the test chamber 206 in a leak free manner.

A collateral pressure-sensing conduit 269 may be coupled to the sample holder 229 and direct a fluid flow pathway toward a pressure transducer 270 that serves to monitor the differential pressure gradient across the test sample 330 within the sample holder 229. The differential pressure transducers 270 monitor the pressure field across each test sample 230 in the sample holders 229 during the testing cycle. Flexible or rigid tubing 269 is connected to the upper and lower sample adapters 247, 248, with the opposite ends of the conduit 269 being connected to the differential pressure transducer 270. Additional monitoring transducers can be introduced through the sensor ports 221 and other ports built into the return chamber 236 as necessary.

Once the fluid flow has exited the sample holders 229 it flows into the return manifold 254 and return chamber 236. The working fluid passes around a throttle valve 232 and a return fluid flow is communicated through return conduit 224 to the lower chamber during a secondary or depressurization portion of the test, thus completing the first portion of the test cycle. The throttle valve 232 is connected to the throttle valve handle 232a, which runs through a fluid-tight fitting on top of compliance chamber cap 221. The throttle valve handle 232a is adjustable, such as by a threaded coupling to the cap 221 on the compliance chamber 235. The throttle valve 232 can be adjusted up or down, increasing or decreasing the resistance to fluid returning to the central return conduit 224 to aid in controlling the differential pressure across the test sample 230. The amount of gas or the elasticity of the elastomeric material inside the compliance chamber 35 allows the user to control the damping of the system and provides an additional tool calibrate the ideal test conditions for the particular prosthetic device. In the embodiment of FIG. 6, a single compliance chamber 235 is axially centered over the test chamber 206 and provides a compliance volume for all of the sample holders 230 in the test chamber 235. Similarly, in this embodiment only a single throttle valve 232 is provided to control the return flow of the working fluid through the center return conduit 224.

Figure 7:
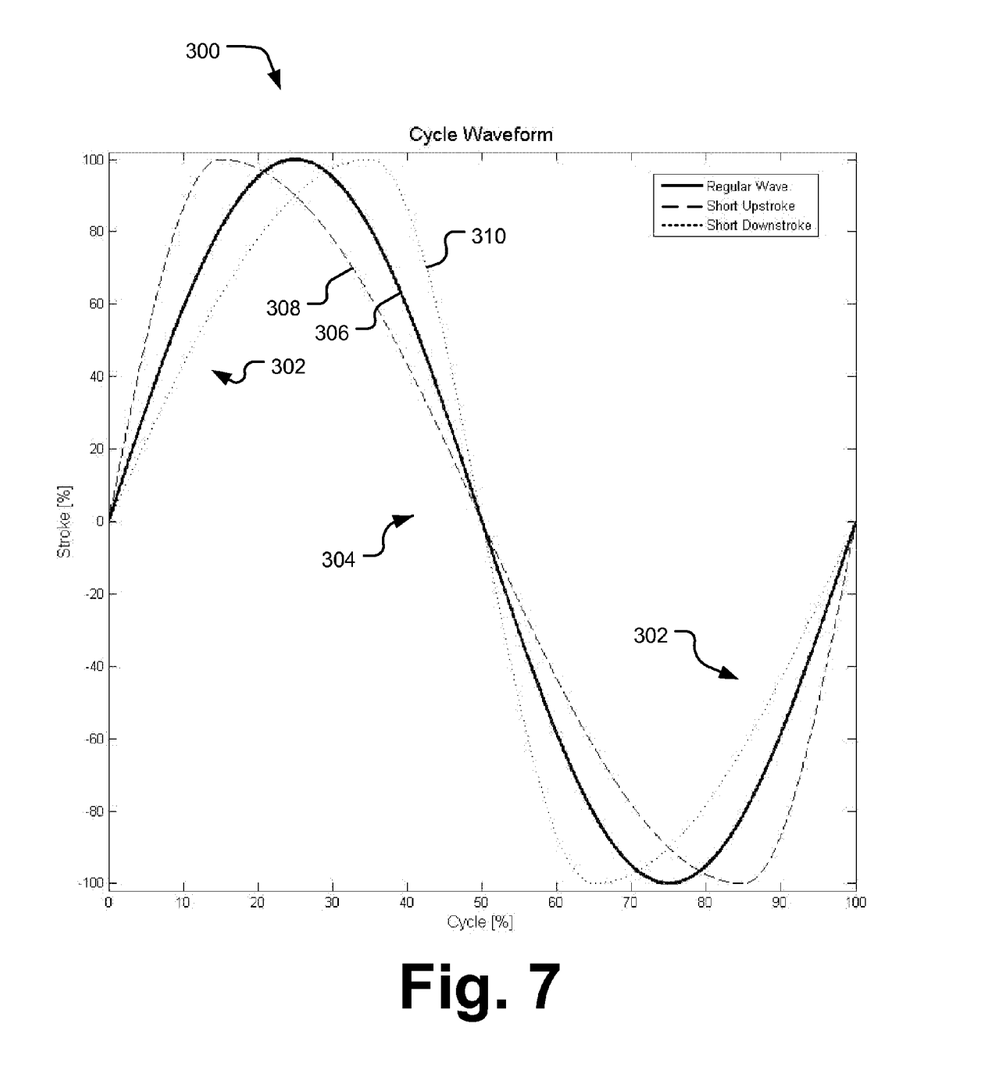
FIG. 7 is a graph depicting three exemplary pressure control waves for generation by test control software to provide pressure across a sample device being tested.

FIG. 7 provides examples of three different pressure control signals generating three different cyclical pressure waveforms 300 across a prosthetic device being tested. Because of the vertical orientation of the displacement components, the term "upstroke" is synonymous with a pressurization stroke of the piston, i.e., that which exerts a positive pressure across the prosthetic device being tested and the term "down stroke" is synonymous with a depressurization stroke of the pump, i.e., that which exerts a negative pressure across the prosthetic device being tested. Typical test systems are only capable of driving the fluid with a regular sine wave 306. A non-regular pressure waveform may be desirable for testing of certain devices as it allows the user to control the rate of pressurization in the test system and optimize the test conditions, while maintaining a desired operating frequency. Two exemplary non-regular waveforms having short upstrokes 308 and down strokes 310, respectively, are illustrated in FIG. 7. However, any arbitrary pressure waveform may be generated and can be utilized to drive the motor and thereby the piston.

During the primary or pressurization portion 302 of the testing cycle, fluid is moved past the prosthesis within the housing tube. In an exemplary implementation in which valve prostheses are tested, the positive upstroke forces the valve prosthesis to the open state. During a secondary or depressurization portion 304 of the test cycle, the flow is reversed and the valve prostheses 30 are closed. As the secondary portion 304 of the cycle begins, the fluid moves through the throttle valves into the central return conduit and back into the distribution chamber through the one-way valve. During return flow, the valve prosthesis remains closed due to the flow reversal and differential pressure present between the distribution chamber and the return chamber. The drive system returns to its starting position and the process is repeated, cycling the prosthetic devices. A single test cycle consists of completion of both the primary portion 302 and secondary portion 304 of the test cycle such that the prosthetic device passes through one open and -closed cycle.

The exemplary pressure waveforms 306, 308, 310 depicted in FIG. 7 may be generated by the fatigue testing system or by other mechanical mechanisms. It is envisioned that alternative mechanical or electromechanical systems, such as those including gearing or cams to drive a pump, may be employed in a manner that generates the variable pressure waveforms as depicted in FIG. 7, in which the pressure gradients are variable over time.

As indicated above, the proposed technology may be integrated with system monitoring and controlling software. The computer software can be used to record and analyze data while controlling the dynamics of the system, as outlined in the exemplary process 400 shown FIG. 8. Data is first obtained by system hardware 402, i.e., the system sensors 406, and then processed though data acquisition hardware 408 and transmitted to the system computer for processing and formatting for presentation by the system software 404.

Figure 8:
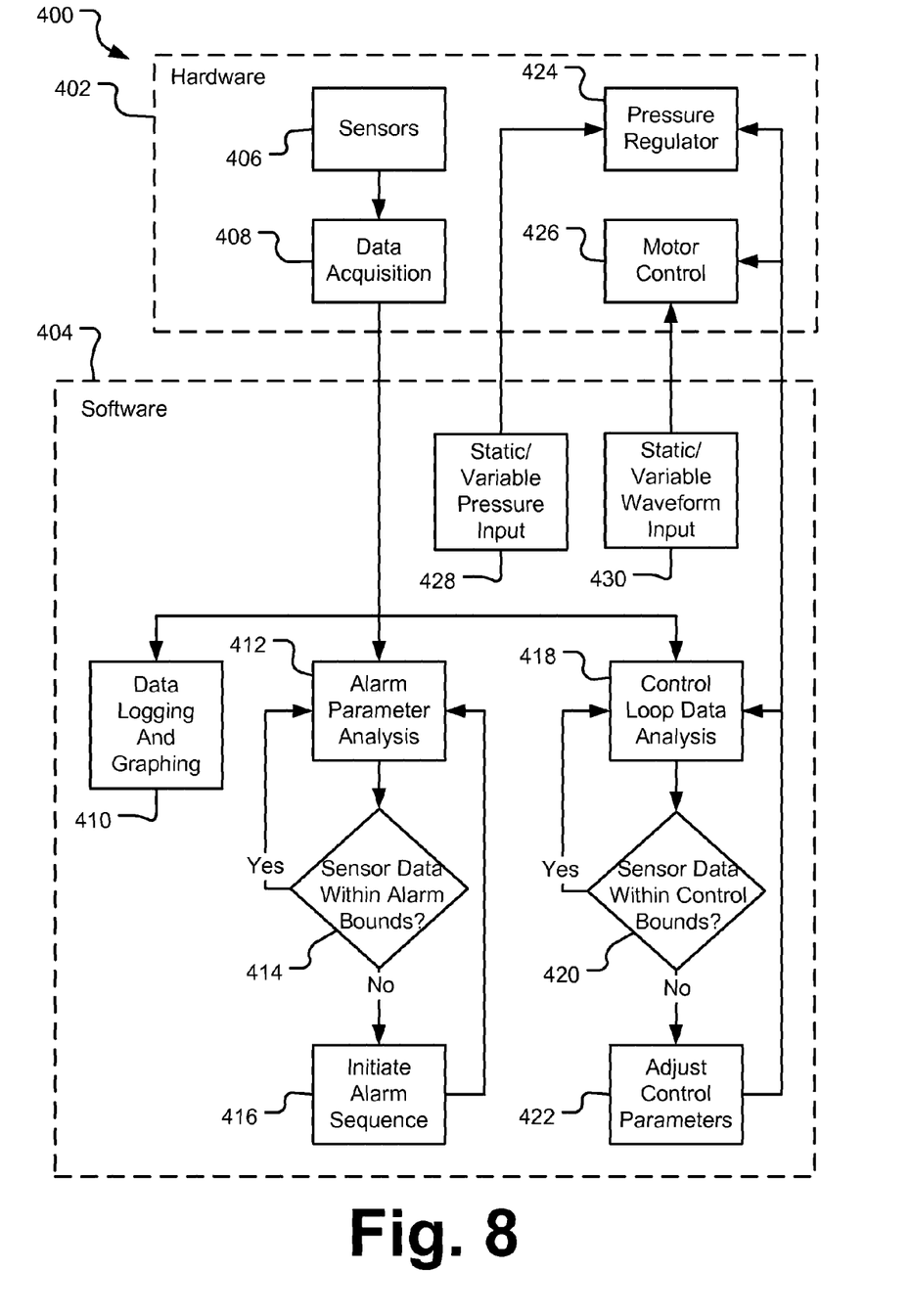
FIG. 8 is a schematic diagram of a software and hardware implementation for controlling a fatigue testing system.

All system inputs and outputs may be continuously monitored and directed into software-based control and alarm system modules, allowing the system to automatically reconfigure or halt if any signal deviates outside of the user set bounds. The real-time data stream may be utilized for three primary purposes: data logging and graphing, alarm condition indication, and test system control. The data logging and plotting subroutine 410 generates graphs and plots of pertinent signals while also creating a data file to allow for test documentation and off-line analysis.

The alarm condition subroutine 412 analyzes data to determine if any of the test inputs or control signals have deviated outside of user defined alarm magnitudes. If an alarm is triggered, i.e. an alarm parameters exceeds its bounds as determined in operation 414, an alarm sequence is initiated as indicated in operation 416. This sequence could trigger a number of events. In one sequence, the software may halt the test system in a specific manner; in another alarm sequence, the test software may notify the operator; in yet another alarm sequence, the system may be halted and the user notified. As can be appreciated, there are a number of actions that are available as part of an alarm sequence and these sequence steps could be dependent on a number of parameters including the specific test samples and/or the specific test protocol.

The control loop subroutine 418 further monitors the control parameters based on a user defined target input signals and/or parameters. Exemplary user set parameters may include pressure input parameters 428 and motor drive waveform parameters 430. Each of these parameters may be set as static or variable. If the control loop determines that the real-time sensor data received is outside the bounds of the user parameters as determined in operation 420, then the software adjusts the input control parameters provided to the hardware control systems as indicated in operation 422. As one example, test system pressure may be set as the control parameter; therefore, the software will continually adjust the dynamics of the pressure regulator 424 to maintain the desired pressure. In another example, the displacement of the driver may be the control parameter; therefore, the software will continually adjust the system dynamics for the motor control 426 to maintain the desired displacement. Again, as one can appreciate, the closed-loop control of the test system can be applied to myriad parameters.

Figure 9:
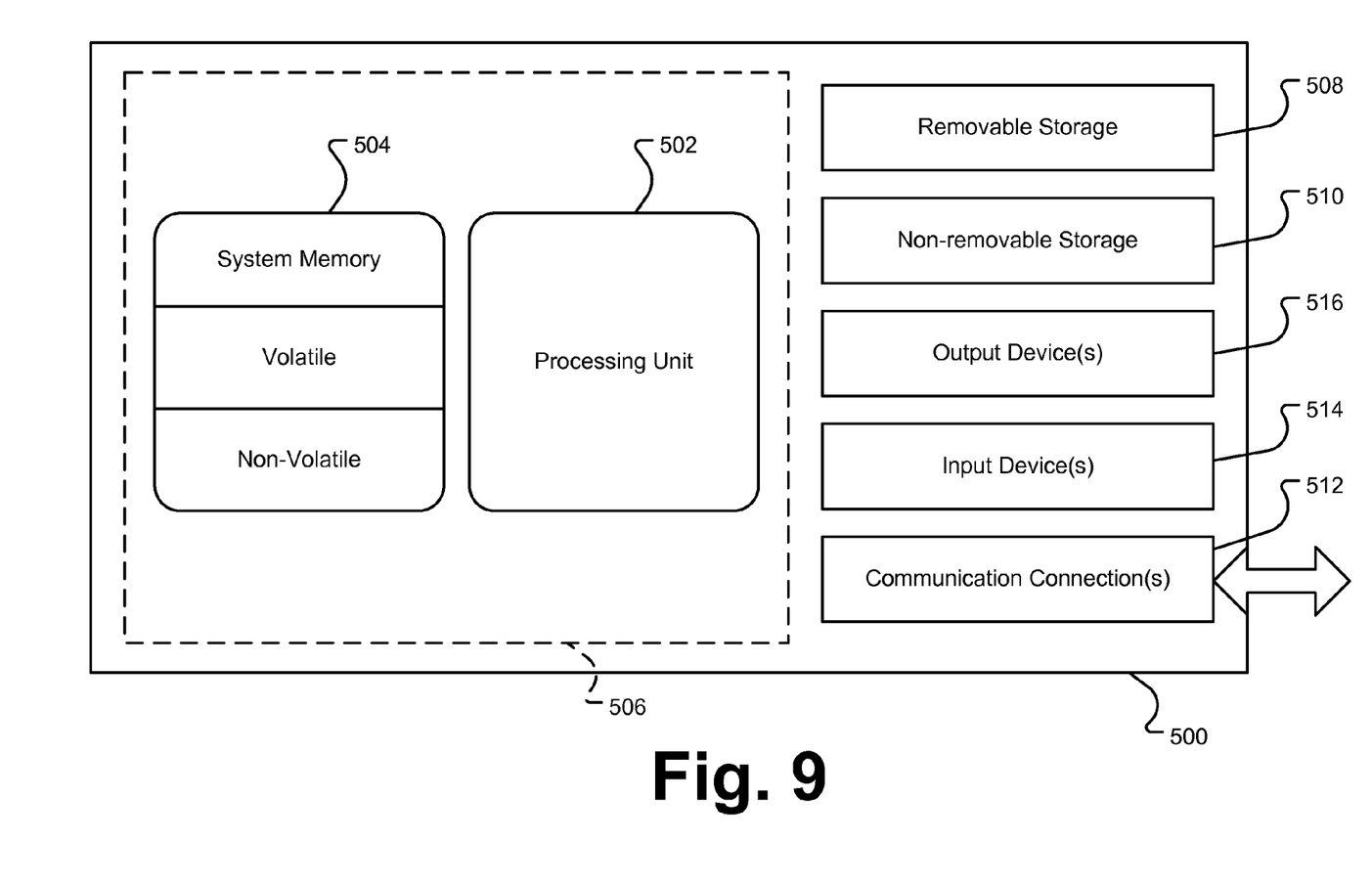
FIG. 9 is a schematic diagram of an exemplary computer system for controlling a fatigue testing system.

FIG. 9 illustrates an exemplary computer system 500 configured as part of the fatigue testing system as described herein. In one implementation, the computer system 500 typically includes at least one processing unit 502 and memory 504. Depending upon the exact configuration and type of the computer system 500, the memory 504 may be volatile (e.g., RAM), non-volatile (e.g., ROM and flash memory), or some combination of both. The most basic configuration of the computer system 500 need include only the processing unit 502 and the memory 504 as indicated by the dashed line 506.

The computer system 500 may further include additional devices for memory storage or retrieval. These devices may be removable storage devices 508 or non-removable storage devices 510, for example, memory cards, magnetic disk drives, magnetic tape drives, and optical drives for memory storage and retrieval on magnetic and optical media. Storage media may include volatile and nonvolatile media, both removable and non-removable, and may be provided in any of a number of configurations, for example, RAM, ROM, EEPROM, flash memory, CD-ROM, DVD, or other optical storage medium, magnetic cassettes, magnetic tape, magnetic disk, or other magnetic storage device, or any other memory technology or medium that can be used to store data and can be accessed by the processing unit 502. Alarm monitoring, data acquisition, and closed loop control software modules may be stored on the storage device for execution by the processing unit 502 using any method or technology for storage of data, for example, computer readable instructions, data structures, and program modules.

The computer system 500 may also have one or more communication interfaces 512 that allow the system 500 to communicate with other devices. The communication interface 512 may be connected with a network. The network may be a local area network (LAN), a wide area network (WAN), a telephony network, a cable network, an optical network, the Internet, a direct wired connection, a wireless network, e.g., radio frequency, infrared, microwave, or acoustic, or other networks enabling the transfer of data between devices. Data is generally transmitted to and from the communication interface 512 over the network via a modulated data signal, e.g., a carrier wave or other transport medium. A modulated data signal is an electromagnetic signal with characteristics that can be set or changed in such a manner as to encode data within the signal.

The computer system 500 may further have a variety of input devices 514 and output devices 516. Exemplary input devices 514 may include sensors, a keyboard, a mouse, a tablet, and/or a touch screen device. Exemplary output devices 516 may include a display and speakers. Such input devices 514 and output devices 516 may be integrated with the computer system 500 or they may be connected to the computer system 500 via wires or wirelessly, e.g., via IEEE 802.11 or Bluetooth protocol. These integrated or peripheral input and output devices are generally well known and are not further discussed herein. Other functions, for example, handling network communication transactions, may be performed by an operating system in the nonvolatile memory 504 of the computer system 500.

The technology described herein may be implemented as logical operations and/or modules in one or more systems. The logical operations may be implemented as a sequence of processor-implemented steps executing in one or more computer systems and as interconnected machine or circuit modules within one or more computer systems. Likewise, the descriptions of various component modules may be provided in terms of operations executed or effected by the modules. The resulting implementation is a matter of choice, dependent on the performance requirements of the underlying system implementing the described technology. Accordingly, the logical operations making up the embodiments of the technology described herein are referred to variously as operations, steps, objects, or modules. Furthermore, it should be understood that logical operations may be performed in any order, unless explicitly claimed otherwise or a specific order is inherently necessitated by the claim language.

In some implementations, articles of manufacture are provided as computer program products that cause the instantiation of operations on a computer system to implement the invention. One implementation of a computer program product provides a computer program storage medium readable by a computer system and encoding a computer program. It should further be understood that the described technology may be employed in special purpose devices independent of a personal computer.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A device for accelerated cyclic testing of a valved prosthetic device comprising
    a pressure source configured to drive a test system fluid cyclically within the device above a normal physiological rate, at an accelerated pulsed rate of greater than 200 beats per minute within the device; and
    a pressurizable test chamber for containing the test system fluid and further comprising
        a fluid distribution chamber positioned on a first side of the valved prosthetic device and in fluid communication with the pressure source;
        a fluid return chamber positioned on a second side of the valved prosthetic device;
        a fluid return conduit both structurally and fluidly connecting the fluid distribution chamber to the fluid return chamber; and
        an excess volume area capable of operating at the accelerated pulsed rate, wherein the excess volume area is in fluid communication with the fluid return chamber providing a volume for storing a volume of a test system fluid when the test system fluid is under compression.

2. The device in claim 1 further comprising
    a drive motor; and
    a fluid displacement member connected with and driven by the drive motor to provide the pressure source that increases and decreases a pressure on the test system fluid in the test chamber.

3. The device of claim 2, wherein the drive motor is configured to operate cyclically, acyclically, or a combination of both, to provide cyclic and acyclic fluid pressures within the test chamber.

4. The device of claim 2, wherein the drive motor comprises a linear motor.

5. The device of claim 2, wherein the fluid displacement member further comprises a flexible rolling bellows connected to a shaft of the drive motor.

6. The device of claim 1, wherein the excess volume area enlarges in response to compression of the test system fluid and decreases during depressurization of the test system fluid.

7. The device of claim 1 further comprising an elastomeric material that forms at least a portion of a boundary of the excess volume area and that expands and contracts in response to changes in pressure on the test system fluid within the test chamber.

8. The device of claim 1, wherein the excess volume area further contains a volume of a compressible gas that is compressed by the volume of the test system fluid to provide a spring force when the volume of the test system fluid is stored in the excess volume area.

9. The device of claim 1, wherein the excess volume area comprises a compliance chamber defining a cavity within the fluid return chamber.

10. The device of claim 9 further comprising an elastomeric membrane separating at least a portion of the compliance chamber from fluid in the fluid return chamber.

11. The device of claim 9 further comprising a porous material at least partially filling the compliance chamber.

12. The device of claim 9, wherein the compliance chamber provides a volume for holding a gas or elastomeric material that compresses under a pressure placed upon the test system fluid in the test chamber and allows the test system fluid in the test chamber to occupy a portion of the volume in the compliance chamber.

13. The device of claim 1, wherein the test chamber defines a first port on a first side of the valved prosthetic device and a second port on a second side of the valved prosthetic device; and
    the first port and the second port are configured to receive one or more sensor devices.

* * * * *